United States Patent [19]

Froment

[11] 4,367,645
[45] Jan. 11, 1983

[54] HOT GAS SAMPLING

[75] Inventor: Gilbert F. Froment, Deurle, Belgium

[73] Assignee: Kinetics Technology International Corporation, Pasadena, Calif.

[21] Appl. No.: 212,583

[22] Filed: Dec. 3, 1980

[51] Int. Cl.³ .................... G01N 31/08; G01N 1/22
[52] U.S. Cl. .................................. 73/23.1; 73/863.72
[58] Field of Search ............... 73/23.1, 863.11, 863.71, 73/863.72, 863.73

[56] References Cited

U.S. PATENT DOCUMENTS

| 3,041,869 | 7/1962 | Spracklen et al. | 73/23.1 |
| 3,201,922 | 8/1965 | Villalobos | 73/23.1 |
| 3,686,923 | 8/1972 | Favre | 73/23.1 |
| 3,798,973 | 3/1974 | Estey | 73/23.1 |

Primary Examiner—Stephen A. Kreitman
Attorney, Agent, or Firm—William W. Haefliger

[57] ABSTRACT

Apparatus and method are provided to achieve efficient on-line sampling of hot effluent gases from high temperature reactors. A heated transfer valve is movable between sampling and injection positions to control carrier gas and sample gas flow to a chromatograph.

13 Claims, 7 Drawing Figures

POSITION: SAMPLING

— FURNACE EFFLUENT
--- CARRIER GAS

POSITION: SAMPLING

POSITION: INJECTION

— FURNACE EFFLUENT
--- CARRIER GAS (+ SAMPLE)

POSITION: INJECTION

HOT GAS SAMPLING

BACKGROUND OF THE INVENTION

This invention relates generally to on-line sampling of hot effluent gases from high temperature reactors; more specifically, it concerns apparatus and method to achieve efficient on-line sampling of such gases.

There is a continuing need for efficient sampling of hydrocarbons, some of which boil at high temperatures so that they condense in the usual sampling devices which are at lower temperatures. Example of such gases are those produced in the thermal cracking for olefin production of hydrocarbon mixtures such as naptha, gasoil, etc. In such processes, the effluent exits from the cracking coil at around 850° C., and typically proceeds to a transfer line heat exchanger with an outlet temperature of about 340° C. The effluent contains steam, hydrogen and hydrocarbons from methane up to components having as many as 20 carbon atoms. It is of importance to sample and analyse such an effluent at frequent intervals under on-line conditions, to obtain up-to-date information as to composition, rather than obtaining its composition from periodic plant balances.

Prior attempts to achieve analysis of such gases include provision of a device that had to be carried to a remote analytical laboratory after receiving a hot gas sample. This and other devices were plagued by condensation of heavy products, causing unwanted fouling or plugging, and frequently leading to incorrect analysis of the effluent.

SUMMARY OF THE INVENTION

It is a major object of the invention to provide a system and valve device overcoming the above as well as other problems associated with prior sampling methods.

Basically, the invention contemplates the obtaining of complete and correct analysis of the hot effluent hydrocarbon gases, avoiding plugging and fouling problems through the provision of apparatus and method employing sampling of small quantities of effluent in apparatus maintained at elevated temperatures, together with high dilution of the sample with carrier gas and pre-separation by means of a coated capillary line leading to a gas chromatograph.

In its apparatus aspects the invention basically employs a transfer valve kept at high temperature and connected to a source of carrier gas and to a gas chromatograph or other analytical equipment over a capillary coated gas chromatograph column of 50 m or more. It is characterized by:

(a) the transfer valve being heated and having multiple inlet ports and multiple outlet ports, (b) there being a sample receiving duct in communication with the valve, (c) the valve having relatively moveable members defining a "sampling" position, and an "injection" position, (d) the "sampling" position characterized in that one inlet port, the sample receiving duct and one outlet port are connected in series to pass the hot gas to a vessel in which bubbling indicates flow through the duct and other inlet and outlet ports are connected in series to pass the carrier gas to the splitter and the analytical equipment and (e) the "injection" position characterized in that said one inlet port and said one outlet port are connected in series to pass the hot gas to the bubbling vessel and said other inlet port, said sample receiving duct and the other outlet port being connected in series with the source of carrier gas to pass a sample of hot gas in the duct to the splitter and the analytical equipment.

As will be seen, a gas chromatograph is connected over a coated capillary gas chromatographic pre-separation column to the splitter to receive a portion of the hot gas from a splitter; the gas chromatograph itself also contains a separation column, of course; the transfer valve and splitter are typically contained in a chamber maintained at elevated temperature; and the transfer valve has six ports, and multiple internal passages respectively connecting pairs of said ports, as will be seen.

For its method aspects, the invention contemplates the steps:

(a) maintaining the valve at elevated temperature, (b) passing a sample of the hot gas stream via the valve into a sampling duct connecting with the valve, (c) passing a carrier gas through a channel in the valve, (d) switching the valve to cause the carrier gas to entrain the sample in said duct, (e) splitting the carrier gas and entrained sample into two streams while both are maintained at elevated temperature, and (f) passing one of the streams to a gas chromatograph through a line which is a coated capillary pre-separation gas chromatograph column kept at 200° C.

These and other objects and advantages of the invention, as well as the details of an illustrative embodiment, will be more fully understood from the following description and drawings, in which:

DRAWING DESCRIPTION

DETAILED DESCRIPTION

Figure 1:
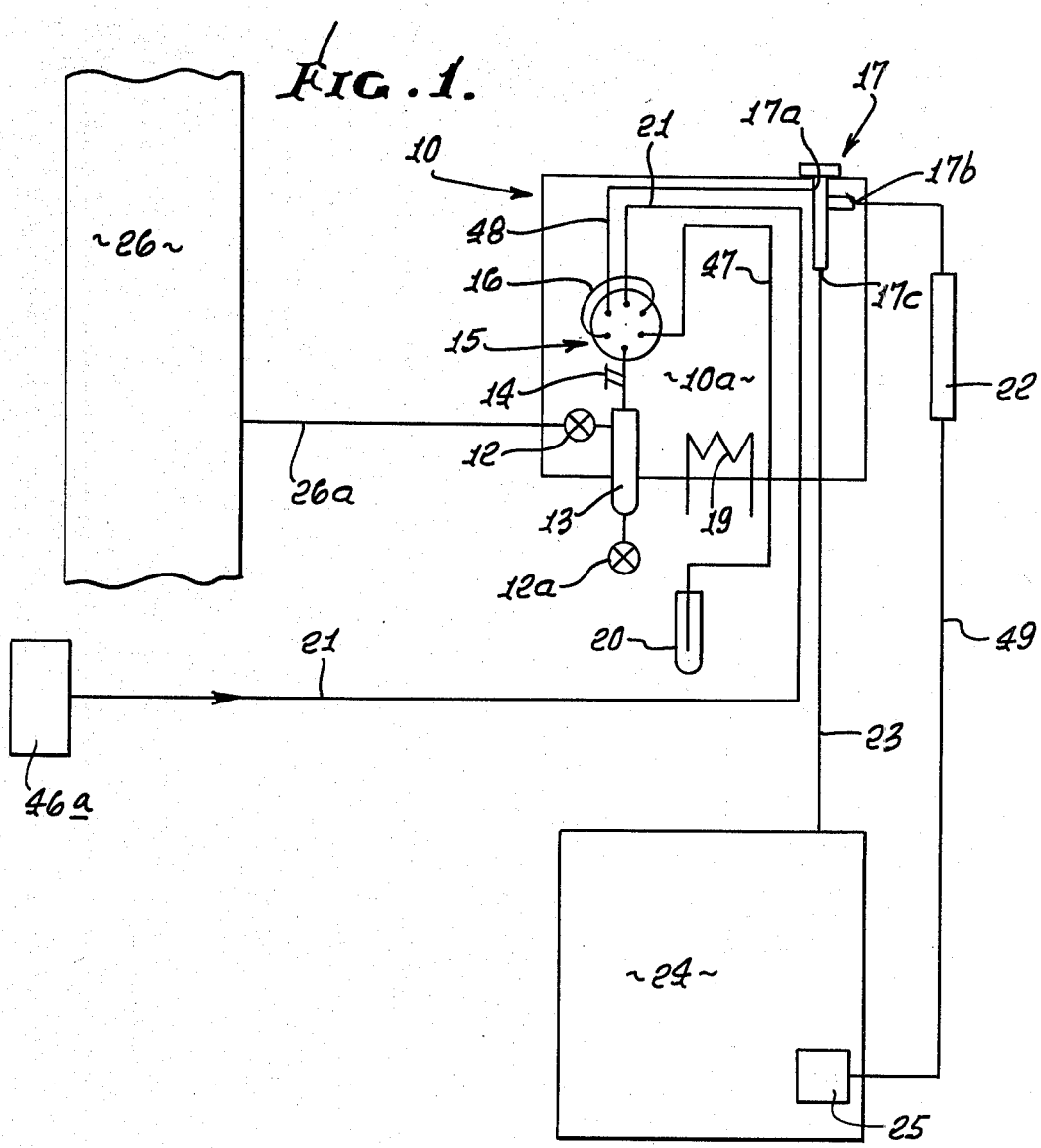
FIG. 1 is a system diagram.

In FIG. 1, a chamber or box 10 is suitably heated as by an electrical heating element 19, as for example a Cal rod. The box interior 10a is typically maintained at about 300° C. Hot gas effluent from sampling line 26 passes via line 26a to a small cyclone 13 via inlet valve 12, the latter elements being in the container heated interior 10a. An outlet valve for tar and coke from the cyclone, is shown at 12a.

Gas to be sampled passes from the cyclone and through a filter 14 (as for example a gauze filter) that removes very small remanent particulate. From that filter the gas to be sampled (i.e. gas such as steam, hydrogen and hydrocarbons having from 1 to 20 carbon atoms) enters a transfer valve 15, which is also heated by virtue of its location within the heated interior 10a of the chamber 10.

Figure 2:
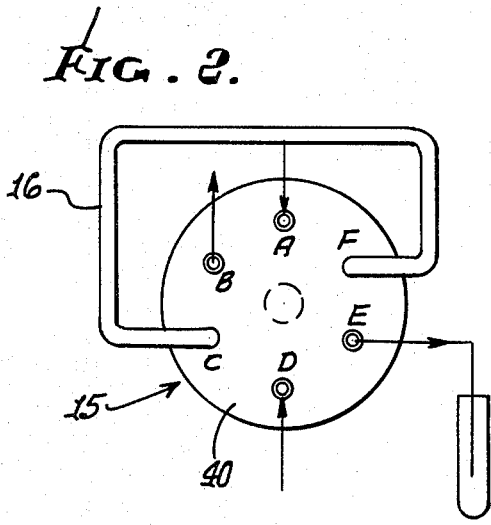
FIG. 2 is a detailed frontal view of one form of valve as usable in the FIG. 1 system.
Figure 6A:
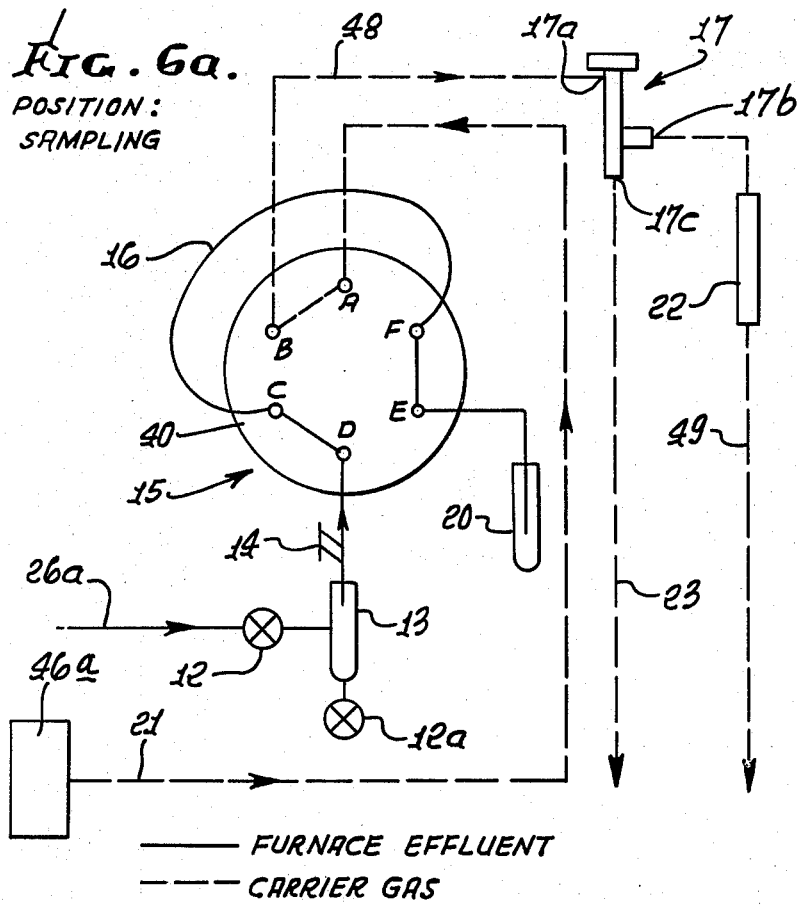
FIG. 6a is a system diagram showing the valve of FIGS. 2 and 5 in frontal view and in "sampling" position.
Figure 6B:
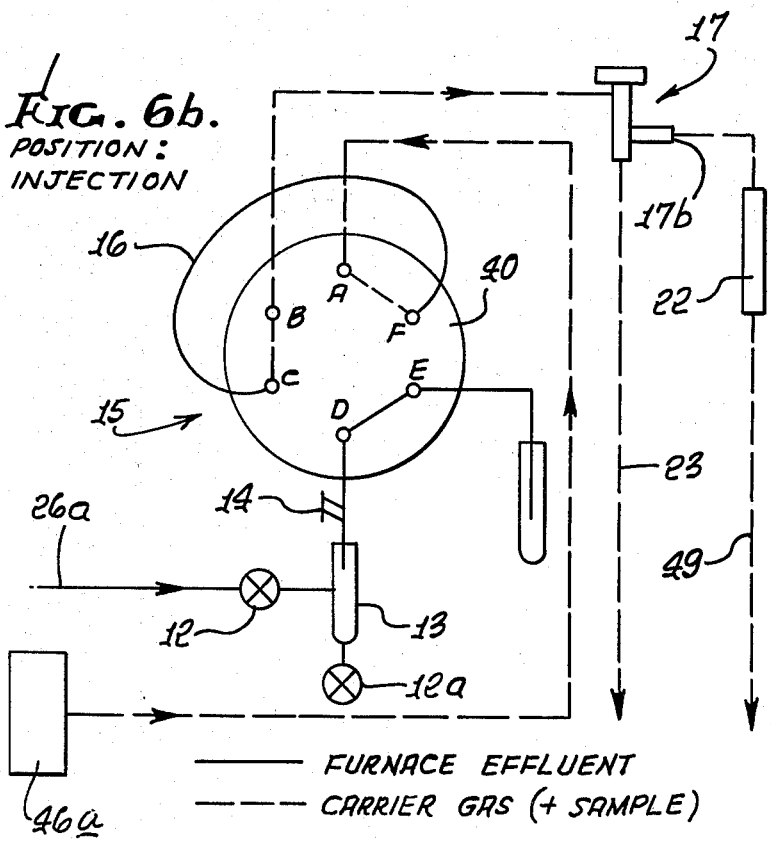
FIG. 6b is a system diagram like FIG. 6a, showing the valve in "injection" position.

Valve 15, which may take various forms, is characterized as having multiple inlet ports (as for example at A and D as shown in FIGS. 2, 6a and 6b) and multiple outlet ports (as for example at B and E as shown in FIGS. 2, 6a and 6b). Such ports are typically located in a valve member 40 which is relatively non-rotatable. That member also has ports as at C and F that are in communication with a sample receiving duct 16 external to the valve (but within chamber heated interior 10a) and of predetermined length corresponding to the volume of sample gas to be analysed. Accordingly, the valve 15 is characterized as having six ports, identified at A-F.

Figure 3:
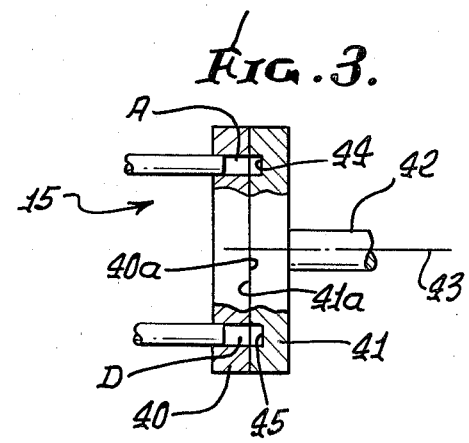
FIG. 3 is a partially cut away side view of the FIG. 2 valve.
Figure 4:
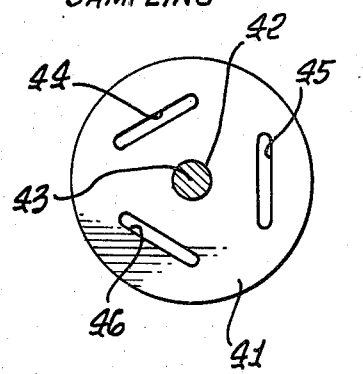
FIG. 4 is a frontal view of a relatively rotatable member of the valve depicted in FIGS. 2 and 3, and in "sampling" position.
Figure 5:
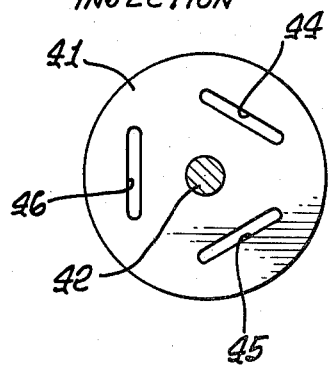
FIG. 5 is a view like FIG. 4 showing the member in relatively rotated "injection" position.

FIGS. 3-5 also shows a relatively rotatable valve member 41, with means 42 for rotating same about central axis 43, so as to provide a "sampling" position of the valve as well as an "injection" position. Such rotation is through a 60° angle, allowing very quick adjustment rotation of the valve. Member 41 has a face 41a slidably engaging face 40a of member 40, the drawings showing that ports A-F pass through member 40 and intersect the interfaces 40a and 41a. Further, member 41 contains three transfer passages 44-46 spaced about axis 43 and of lengths to communicate between pairs of the ports A-F in each of the "sample" and "inject" positions referred to.

Referring to FIGS. 1, 6a and 6b, a source of "carrier" gas is shown at 46a, and is connected via line 21 with port A. A typical carrier gas is nitrogen.

.Port E is connected via line 47 with a receiver vessel 20 containing liquid, such as water, whereby gas leaving port E is detected by bubbling of liquid in vessel 20. The latter is shown as outside chamber 10. Port B is connected via line 48 with a "splitter" 17 having inlet 17a and outlets 17b and 17c. Splitter 17 is located in chamber 10, and functions to remove a portion of the gas to be sampled, for delivery at 17c along with carrier gas to a capillary coated gas chromatograph column 23. The latter is associated with gas chromatograph apparatus 24, having an associated flow control 25. The latter may take the form of a valve to pass the side gas stream delivered at 17b and passing through "active" charcoal filter 22, wherein sample gas is adsorbed and carrier gas flows through 49 to the controller 25. The adjustment of the latter is such as to achieve a constant gas split ratio, as between gas delivered at ports 17b and 17c.

The column 23 pre-separates the sample into its components prior to injection into the gas chromatograph 24, also containing an appropriate capillary coated column.

In operation, the valve 15 is first adjusted as by rotation of member 41 to FIG. 5 position (see also FIG. 6b), for flushing of the duct 16. Valve 12 is then opened. Effluent gas then flows via line 26a, cyclone 13, filter 14 and via ports D and E and transfer passage 45 to vessel 20. Carrier gas flows via port A, transfer passage 44, port F, duct 16, port C, transfer passage 46, port B and line 48 to splitter 17 and column 23 and line 49.

Subsequently, the six-way valve 15 is switched or adjusted into sampling position (see FIGS. 4 and 6a) for a predetermined short interval, such as about 5 seconds (for best results). In that position, the furnace effluent flows via valve 12, cyclone 13 and filter 14 to port D. From the latter, the effluent gas to be sampled passes via transfer passage 46, port C, through the sample loop or duct 16, port F, transfer passage 45, port E and line 47 to bubble vessel 20. Bubbling at the end of the interval indicates that duct 16 contains a predetermined volume of sample gas, without carrier gas being present. Meanwhile, carrier gas flows via port A, transfer passage 44, port B and line 48 to splitter 17. From the latter, carrier gas flows via column 23 into chromatograph 24.

After the predetermined interval, the valve 15 is switched or adjusted to FIG. 6b position (see also FIG. 5), for the injection stage which lasts for another predetermined interval (about 10 seconds, for best results). In that position, the carrier gas enters the valve via port A, travels via transfer passage 44 to port F and enters duct 16 to drive the sample in the latter out through port C, passage 46 and port B. From the latter, the sample is driven to the splitter 17, through column 23 and to chromatograph 24. Typically, only about one percent of the gas contained in the sample duct 16 flows in this manner, ninety-nine percent being diverted by the splitter through outlet 17b, filter 14 and to controller 25, which enables constant flow rates to be established in both lines 23 and 49 leaving the splitter. Effluent gas at this time passes via D, 45, E and 47 to receiver 20. After the injection stage, the valve 12 is closed.

Examples of elements 15, 23, 24 and 25 are as follows:

| Element | Manufacturer | Model |
|---|---|---|
| 15 | VALCO Instruments Houston, Texas | CV-6-HTa |
| 23 | Supelco Inc. Bell Fontaine, Pa. | OV 101 |
| 24 | Packard Instrument Co. Burlingame, California | 428 |
| 25 | Packard Instrument Co. Burlingame, California | 511 |

I claim:

1. An apparatus for sampling a stream of hot gas containing hydrocarbons, and employing a heated transfer valve, a source of carrier gas for sampling and diluting the hot gas and transferring it over a hot capillary coated pre-separation column to analytical equipment, a gas splitter and a gas receiver, the improvement comprising
   (a) said transfer valve being heated and having multiple inlet ports and multiple outlet ports,
   (b) there being a sample receiving duct in communication with said valve,
   (c) said valve having relatively movable members defining a sampling position, and an injection position,
   (d) said sampling position characterized in that one inlet port, the sample receiving duct and one outlet port are connected in series to pass said hot gas to said receiver, and other inlet and outlet ports are connected in series to pass the carrier gas to the analytical equipment through the splitter and a hot line which is a pre-separation coated capillary column,
   (e) said injection position characterized in that said one inlet port and said one outlet port are connected in series to pass said hot gas to the receiver, and said other inlet port, said sample receiving duct and said other outlet port are connected in series with said source of carrier gas to pass a sample of hot gas in said duct to the analytical equipment through the splitter and a hot line which is a pre-separation coated capillary column, (f) a gas chromatograph connected in series with the splitter to receive a portion of the hot gas sample from the splitter, and (g) a side passage connected with the splitter to pass split carrier gas toward a flow controller.

2. The apparatus of claim 1 including a gas chromatograph connected in series with the splitter to receive a portion of the hot gas sample from the splitter.

3. The apparatus of claim 1 including a heated chamber or box or container means in which said valve and said splitter are received.

4. The apparatus of claim 3 including means to maintain the interior of said chamber or box or container means at about 300° C.

5. The apparatus of claim 1 including a cyclone connected in series with said one inlet port.

6. The apparatus of claim 1 including said hot gas to be sampled in said duct, and consisting of hydrocarbons, $H_2O$, hydrogen or other chemical compounds.

7. The apparatus of claim 1 wherein said transfer valve has two additional ports connected with said duct, whereby the valve has six ports, the valve also having three internal passages respectively connected with pairs of said ports in each of said sampling and injection positions.

8. An apparatus for sampling a stream of hot gas containing hydrocarbons, and employing a heated transfer valve, a source of carrier gas for sampling and diluting the hot gas and transferring it over a hot capillary coated pre-separation column to analytical equipment, a gas splitter and a gas receiver, the improvement comprising (a) said transfer valve being heated and having multiple inlet ports and multiple outlet ports, (b) there being a sample receiving duct in communication with said valve, (c) said valve having relatively movable members defining a sampling position, and an injection position, (d) said sampling position characterized in that one inlet port, the sample receiving duct and one outlet port are connected in series to pass said hot gas to said receiver, and other inlet and outlet ports are connected in series to pass the carrier gas to the analytical equipment through the splitter and a hot line which is a pre-separation coated capillary column, (e) said injection position characterized in that said one inlet port and said one outlet port are connected in series to pass said hot gas to the receiver, and said other inlet port, said sample receiving duct and said other outlet port are connected in series with said source of carrier gas to pass a sample of hot gas in said duct to the analytical equipment through the splitter and a hot line which is a pre-separation coated capillary column, (f) a gas chromatograph connected in series with the splitter to receive a portion of the hot gas sample from the splitter, (g) and including a side passage connected with the splitter to pass split carrier gas toward a flow controller after removal of another portion of the sample by means of an active charcoal filter.

9. The apparatus of claim 8 including said flow controller associated with said gas chromatograph and which has a capillary coated pre-separation column via which a small fraction of the sample gas is delivered to the gas chromatograph at a predetermined flow rate controlled by the controller.

10. An apparatus for sampling a stream of hot gas containing hydrocarbons, and employing a heated transfer valve, a source of carrier gas for sampling and diluting the hot gas and transferring it over a hot capillary coated pre-separation column to analytical equipment, a gas splitter and a gas receiver, the improvement comprising (a) said transfer valve being heated and having multiple inlet ports and multiple outlet ports, (b) there being a sample receiving duct in communication with said valve, (c) said valve having relatively movable members defining a sampling position, and an injection position, (d) said sampling position characterized in that one inlet port, the sample receiving duct and one outlet port are connected in series to pass said hot gas to said receiver, and other inlet and outlet ports are connected in series to pass the carrier gas to the analytical equipment through the splitter and a hot line which is a pre-separation coated capillary column, (e) said injection position characterized in that said one inlet port and said one outlet port are connected in series to pass said hot gas to the receiver, and said other inlet port, said sample receiving duct and said other outlet port are connected in series with said source of carrier gas to pass a sample of hot gas in said duct to the analytical equipment through the splitter and a hot line which is a pre-separation coated capillary column, (f) a heated chamber or box or container means in which said valve and said splitter are received, said receiver comprising a liquid containing vessel into which the discharge from said one outlet port is connected, said vessel located outside said heated chamber or box or container means.

11. In a process for sampling a stream of hot gas containing hydrocarbons having 1–20 carbon atoms, and employing a transfer valve, that includes (a) maintaining said valve at elevated temperature, (b) passing a sample of the hot gas stream via the valve into a sampling duct communicating with the valve, (c) passing a carrier gas through a channel in the valve, (d) switching the valve to cause the carrier gas to entrain the sample in said duct, (e) splitting the carrier gas and/or entrained sample into two streams while both are maintained at elevated temperature, and (f) passing one of the streams to an analytical equipment strongly diluted by the carrier gas through a pre-separation capillary coated gas chromatograph column kept at a temperature of at least 200° C., and (g) passing the effluent of said column into a gas chromatograph for further separation and determination of the gas composition, by itself or in connection with a mass spectrometer, (g) and passing the other of said streams toward a flow controller.

12. The method of claim 11 including passing the other of the split streams to a control which controls the ratio of the two streams.

13. The method of claim 11 including providing a heated chamber containing said zone, and carrying out said splitting in said chamber.

* * * * *